(12) United States Patent
Clout et al.

(10) Patent No.: US 12,738,371 B2
(45) Date of Patent: Sep. 15, 2026

(54) SYSTEMS AND METHODS FOR RETRIEVING PART SERVICE HISTORY DURING SERVICING OF A MEDICAL DEVICE

(71) Applicant: KONINKLIJKE PHILIPS N.V., Eindhoven (NL)

(72) Inventors: Ramon Antoine Wiro Clout, Eindhoven (NL); Johannes Henricus Maria Korst, Eindhoven (NL); Mauro Barbieri, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/700,308

(22) PCT Filed: Oct. 13, 2022

(86) PCT No.: PCT/EP2022/078555
§ 371 (c)(1),
(2) Date: Apr. 11, 2024

(87) PCT Pub. No.: WO2023/066789
PCT Pub. Date: Apr. 27, 2023

(65) Prior Publication Data

US 2024/0428932 A1 Dec. 26, 2024

Related U.S. Application Data

(60) Provisional application No. 63/257,276, filed on Oct. 19, 2021.

(51) Int. Cl.
*G16H 40/40* (2018.01)
*A61B 90/92* (2016.01)
(Continued)

(52) U.S. Cl.
CPC ............. *G16H 40/40* (2018.01); *A61B 90/92* (2016.02); *A61B 90/98* (2016.02);
(Continued)

(58) Field of Classification Search
CPC ........ G16H 40/40; A61B 90/92; A61B 90/98; G06K 19/06028; G06K 19/06037; G06K 19/0723; G06Q 10/087
See application file for complete search history.

(56) References Cited

U.S. PATENT DOCUMENTS

2009/0309726 A1* 12/2009 Fritchie .................. G16H 40/40 340/568.1
2013/0087609 A1 4/2013 Nichol
(Continued)

FOREIGN PATENT DOCUMENTS

CN 107622790 A * 1/2018
JP 2006221306 A 8/2006
JP 2008287627 A 11/2008

OTHER PUBLICATIONS

Meng et al. "RFID Medical Equipment Tracking System Based on a Location-Based Service Technique." Journal of Medical and Biological Engineering. vol. 39, pp. 163-169 (2019) (Year: 2019).*
(Continued)

*Primary Examiner* — Linh Giang Le

(57) ABSTRACT

A medical device (120) includes a component (121); and a service tag (130) to be affixed to the component, the service tag having encoded data (134) disposed thereon about servicing of the component of the medical device. In some embodiments, the encoded data includes a summary of a service report or an entire service report reporting on a prior service call, with information such as date of service, information on symptoms related to a problem addressed by the service call, information on one or more service actions performed during the service call, or so forth. In some
(Continued)

embodiments, the encoded data (134) of the service tag (130) comprises one of: a bar code, a quick response (QR) code, and a radiofrequency identification (RFID) code.

8 Claims, 2 Drawing Sheets

(51) Int. Cl.

| | |
|---|---|
| ***A61B 90/98*** | (2016.01) |
| *G06K 19/06* | (2006.01) |
| *G06K 19/07* | (2006.01) |

(52) U.S. Cl.
CPC . *G06K 19/06028* (2013.01); *G06K 19/06037* (2013.01); *G06K 19/0723* (2013.01)

(56) References Cited

U.S. PATENT DOCUMENTS

| | | | | |
|---|---|---|---|---|
| 2013/0222116 | A1* | 8/2013 | Barry, III ............... | G16H 40/20 340/10.1 |
| 2014/0263674 | A1 | 9/2014 | Cerveny | |
| 2017/0083671 | A1 | 3/2017 | Benner | |

OTHER PUBLICATIONS

International Search Report and Written Opinion Dated Feb. 9, 2023 for International Application No. PCT/EP2022/078555 Filed Oct. 13, 2022.

* cited by examiner

SYSTEMS AND METHODS FOR RETRIEVING PART SERVICE HISTORY DURING SERVICING OF A MEDICAL DEVICE

CROSS REFERENCE TO RELATED APPLICATIONS

This application is the U.S. National Phase application under 35 U.S.C. § 371 of International Application No. PCT/EP2022/078555 filed Oct. 13, 2022, which claims the benefit of U.S. Provisional Patent Application No. 63/257,276 filed Oct. 19, 2021. These applications are hereby incorporated by reference herein.

FIELD

The following relates generally to the medical device maintenance arts, medical imaging device maintenance arts, medical device maintenance and task distribution arts, and related arts.

BACKGROUND

Customer services for medical systems, such as magnetic resonance imaging (MRI), computed tomography (CT), positron emission tomography (PET), interventional radiology (IR), or other medical imaging systems, can include reactive, proactive, and predictive maintenance services. Because these services rely heavily on data, availability of a reliable infrastructure that acquires, processes and stores data from medical systems and other sources is crucial. When there is a problem with a medical system, the customer can report the issue to a customer service center via various channels (e.g., by phone, customer portal or mobile application). Then, service engineers (SEs—which can include remote SEs (RSEs) and field SEs (FSEs)) can perform system diagnostics to identify the root-cause of the problem and resolve the issue. Both activities may be performed remotely or on-site, possibly by different SEs. In addition to reactive maintenance as described above, proactive, and predictive diagnostic models are built to identify failure of a system or a part of a system. These models typically process log data of the medical imaging device that is uploaded to the customer service center server, and the output of the diagnostic models is communicated to RSEs, in the form of alerts, predictions of time-to-failure for critical components, or so forth, using a service delivery platform. The RSEs act on the alerts to provide maintenance services.

To assist in the maintenance, parts of medical imaging devices may be tagged with model and/or serial number information. This is useful for tracking inventory, and may also enable identifying issues with specific components. For example, if a manufacturing lot of a part with a known serial number range is defective then the serial number can be useful in recalling the parts. Model number is useful in various ways, such as to determine compatibility of parts with specific imaging systems and/or with other parts, and to determine information such as design-basis limits for that model. Typically, an SE can enter the model information into a parts ordering system to retrieve such model-level information.

The following discloses certain improvements to overcome these problems and others.

SUMMARY

In one aspect, a medical device includes a component, and a service tag to be affixed to the component. The service tag has encoded data disposed thereon about servicing of the component of the medical device. The encoded data of the service tag includes one or more of: an identification of the service action, a summary of a service report or the entire service action report reporting on a prior service call, and/or an employee identification number of an employee who affixed the tag to the associated part.

In another aspect, a method for servicing an associated component of an associated medical device includes generating a service tag for a service call having encoded data disposed thereon about servicing of the associated part of the associated medical device during the service call including at least information about at least one service action performed during the service call; affixing the service tag to the associated part; and with an electronic processing device, reading the encoded data disposed on the service tag including at least the information about the at least one service action performed during the service call.

In another aspect, a medical device maintenance system includes a database storing a plurality of service reports, and a printing device configured to print a service tag to be affixed to an associated component of an associated medical device. The service tag has encoded data disposed thereon about servicing of the associated component of the associated medical device. An electronic processing device comprises a display device and an electronic processor programmed to read the encoded data on the service tag; retrieve, based on the encoded data, a service report related to a prior service action for the service tag from the database; and display the service report on the display device.

One advantage resides in tagging components of medical devices with tags related to servicing of the components.

Another advantage resides in tracking different service actions on parts of a medical devices.

Another advantage resides in tracking cleaning and/or calibration operations on components of medical devices.

Another advantage resides in tagging components of medical devices with color-coded tags, where the colors relate to different service actions of the component.

A given embodiment may provide none, one, two, more, or all of the foregoing advantages, and/or may provide other advantages as will become apparent to one of ordinary skill in the art upon reading and understanding the present disclosure.

BRIEF DESCRIPTION OF THE DRAWINGS

The disclosure may take form in various components and arrangements of components, and in various steps and arrangements of steps. The drawings are only for purposes of illustrating the preferred embodiments and are not to be construed as limiting the disclosure.

DETAILED DESCRIPTION

Figure 1:
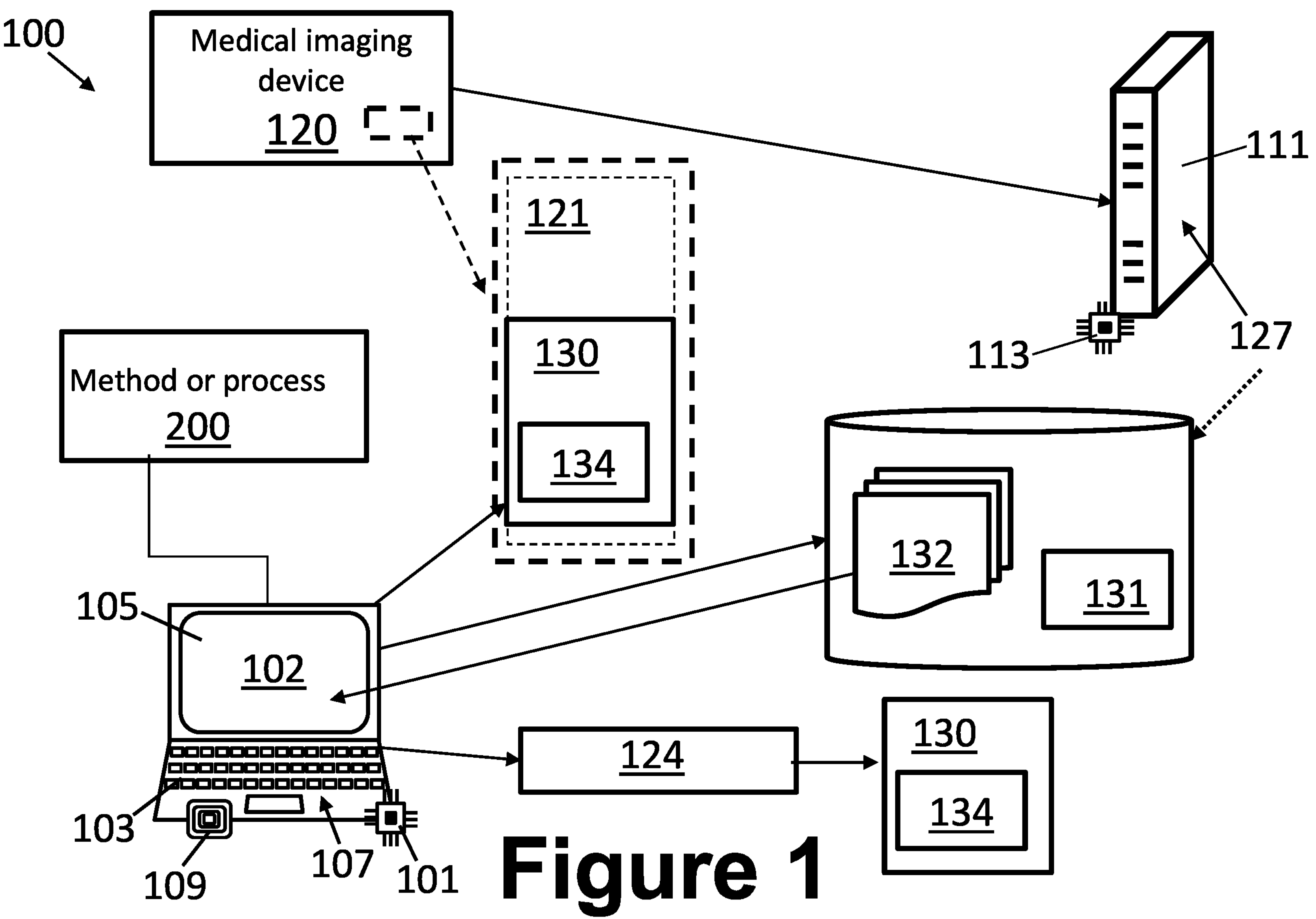
FIG. 1 diagrammatically illustrates an illustrative system for servicing a medical device in accordance with the present disclosure.

As previously noted, serial and model number information can be useful information to a SE during a service call. However, part serial number/model tagging is not well suited for tracking servicing of parts. In some cases, the SE may fail to record the serial number of serviced parts in the service action report, either because the SE failed to appreciate the value in doing so or simply due to inadvertent omission. Furthermore, even if the service action report includes the serial number, it may be difficult for this information to be retrieved during a subsequent service action. A given service action typically involves work on many parts that may (or may not) be related to the problem being serviced, and attempting to query the service actions database with the serial number of each possibly relevant part is tedious and unlikely to be done.

The following discloses providing for service action tags to be affixed to parts that are serviced during a service call. The service action tags have encoded data disposed thereon about servicing of the component of the medical device. This effectively addresses the difficulties mentioned above. First, the service action tag is easily recognized and noticed (for example, in some embodiments it may be a red or other bright color). Thus, the service engineer performing a subsequent service action immediately will see the service action tag(s) on previously serviced part(s), and will also know that any parts that do not have a service action tag have not been previously serviced.

Second, the service action tag preferably includes a bar code, QR code, radio frequency identification (RFID) tag, near-field communication (NFC) tag, or the like which is optically or electronically readable. The bar code, QR code, RFID tag, NFC tag, et cetera records relevant information about servicing history, typically including, for example, an employee identification number or similar information identifying the service engineer who placed the service action tag, a timestamp identifying when the service action took place, a service action identifier that identifies the service action during which the service action tag was placed, and/or so forth. In a variant embodiment, a uniform resource identifier (URI) pointing to this information stored in the cloud can be encoded. Given the large amount of information that can be stored in a QR code or the like, the service action tag may optionally include additional information such as a summary of the service action report or even the entire service action report.

In addition to the service action tags, the disclosed system includes a user interface (UI) that is optionally linked with the service actions database. The UI runs on a notebook computer, cellphone, tablet computer, or other mobile device that includes a barcode reader, QR code reader, RFID tag reader, or the like, via which the service action tag can be easily read. If the service action tag stores a URI or other information linking to an external service history record, the UI then queries the service actions database with the information read from the tag and thereby retrieves the service action report for the prior service action that placed the service action tag, and displays it for the service engineer handling the current service action. In other embodiments, all of the service action history may be stored on the tag itself, so that no link to an external record is needed. This is feasible given the high capacity of QR codes and some other types of information encoding. In these embodiments, it is contemplated for the UI to be, for example, a generic QR code reader application program (app) running on a cellphone or other mobile device.

The service action tags can be stickers that are adhesively affixed to a part, or can be affixed using plastic zip lock strips or other fastening mechanisms. The choice of fastening mechanism may depend on the type and nature of the part, e.g., a part that gets hot may not be amenable to having a sticker placed on it. If affixing the service action tag directly to the part is not feasible (for example, in the case of an internal part of a sub-assembly), then the service action tag may be affixed to the sub-assembly containing the part. (In this case, the serviced part may be viewed as the sub-assembly).

The service action tags can be printed ahead of a service call and carried with the service engineer to the service site. In this case the tags cannot contain the information about the service action report (which has not yet been generated), but can contain information about a work order, or the service engineer and the (planned) time/date of the service action. Alternatively, a small label printer can be carried and used to print the labels on-site. If a part is serviced a second time, then the old service action tag can be removed, or the new sticker can be affixed on top of the old service action tag.

With reference to FIG. 1, an illustrative servicing support or maintenance system 100 for supporting a service engineer in servicing a device 120 (e.g., a medical imaging device—also referred to as a medical device, an imaging device, imaging scanner, and variants thereof) is diagrammatically shown. By way of some non-limiting illustrative examples, the medical imaging device under service may be a magnetic resonance imaging (MRI) scanner, a computed tomography (CT) scanner, a positron emission tomography (PET) scanner, a gamma camera for performing single photon emission computed tomography (SPECT), an interventional radiology (IR) device, or so forth. (More generally, the disclosed approach can be applied in conjunction with any type of computerized device that automatically generates log data that are analyzed by predictive models to predict component failures, e.g., the approach could be applied to servicing of components of a commercial airliner, radiation therapy device, or so forth).

As shown in FIG. 1, the maintenance system 100 includes, or is accessible by, a service device 102 that may for example be a workstation or electronic processing device used by an RSE. The service device 102 may for example be a portable device such as a notebook computer that is carried or accessed by an RSE. The service device 102 can be a desktop computer or a personal device, such as a mobile computer system such as a laptop or smart device. In other embodiments, the service device 102 may be an imaging system controller or computer integral with or operatively connected with the imaging device undergoing service (e.g., at a medical facility). As another example, the service device 102 may be a portable computer (e.g., notebook computer, tablet computer, or so forth) carried by an RSE performing diagnosis of a fault with the medical device 120 and ordering of parts. In another example, the service device 102 may be the controller computer of the medical device 120 under service, or a computer based at the hospital. In other embodiments, the service device 102 may be a mobile device such as a cellular telephone (cellphone) or tablet computer.

The service device 102 includes a display 105 via which alerts generated by predictive failure models are displayed, along with likely root cause and service action recommendation information as disclosed herein. The service device 102 also preferably allows the service engineer to interact with the servicing support system via at least one user input device 103 such as a mouse, keyboard, or touchscreen. The service device further includes an electronic processer 101 and non-transitory storage medium 107 (internal components which are diagrammatically indicated in FIG. 1). The non-transitory storage medium 107 stores instructions which are readable and executable by the electronic processor 101 for interfacing with the servicing support or maintenance system 100. The service device 102 also includes a communication interface 109 to communicate with a backend server or processing device 111, which typically implements the computational aspects of the servicing support system 100 (e.g., the server 111 has the processing power for implementing computationally complex aspects of the servicing support system 100). Such communication interfaces 109 include, for example, a wired and/or wireless Ethernet interface (e.g., in the case in which the service device 102 is a RSE workstation); or in the case in which the service device 102 is a portable FSE device the interface 109 may be a wireless Wi-Fi or 4G/5G interface or the like for connection to the Internet and/or an intranet. Some aspects of the servicing support or maintenance system 100 may also be implemented by cloud processing or other remote processing (that is, the server computer 111 may be embodied as a cloud-based computing resource comprising a plurality of interconnected servers). If all service information is stored on the tag, with no embedded URI or other link to any external database of servicing information, then the communication interface 109 and backend server or processing device 111 may optionally be omitted.

During a current service case for the medical device 120, one or more service tags 130 can be utilized. Typically, the current service case involves the FSE servicing a component 121 of the medical device 120 (in a particular example, the medical device 120 can be a medical imaging device 120, and the component 121 can be an X-ray tube of the medical imaging device 120). The service tag 130 is configured to be affixed to the component 121 after the FSE has finished servicing the component 121. In some examples, the service tag 130 includes an adhesive to be affixed to the component 121, or to a system containing the component 121 (i.e., a portion of a housing of the medical device 120 that includes the component 121). That is, when the component 121 to be repaired is a component of a larger subsystem of the medical device 120, then the component 121 can be considered the larger subsystem. In other examples, the service tag 130 can include a fastening mechanism (e.g., plastic zip lock strips, hooks-and-loops, rings, magnets, and so forth) to be affixed to the component 121.

In some embodiments, the service device 102 and/or the medical device 120 can be electronically or wirelessly connected with an electronic database 111. The database 111 receives log data (e.g., a machine log automatically generated by the medical device 120, a service log for the medical device 120, and/or so forth) on a continuous or occasional basis (e.g., in some setups the medical device 120 uploads machine log entries to the database 111 on a daily basis). The database 111 is equipped with an electronic processor 113 and a non-transitory storage medium 127 (internal components which are diagrammatically indicated in FIG. 1). While a single server computer is shown, it will be appreciated that the database 111 may more generally be implemented on a single server computer, or a server cluster, or a cloud computing resource comprising ad hoc-interconnected server computers, or so forth. Furthermore, while FIG. 1 shows a single imaging device 120, more generally the database 111 will receive log data from many medical imaging devices (e.g., tens, hundreds, or more imaging devices) and performs the disclosed processing for each such medical imaging device 120.

In addition, the non-transitory computer readable medium 127 of the database 111 stores one or more service reports 132 related to prior service call for the medical device 120. A service report 132 is typically written by a service engineer during and/or upon completion of a service call conducted to address a problem reported for a medical device. A service report 132 typically includes information about the service call that is the subject of the service report, such as the date of the service call, information on symptoms related to the problem as reported by the customer and/or observed by the service engineer and/or extracted from the machine log of the medical device, information on one or more service actions performed during the service call, new or replacement parts (if any) installed during the service call, results of tests (if any) run during the service call to diagnose the problem and/or verify it has been solved (for example, the test results may include one or more measured component performance or calibration parameters, image quality parameters for a measured imaging phantom used in a test of a medical imaging device, or so forth), and so forth. A service report 132 is typically entered using a standard electronic form (e.g., a web page form) having various structured data entry fields (e.g., drop-down lists, checkboxes, or so forth), semi-structured data entry fields (e.g., a "Replacement parts" field that is constrained to receive only part numbers matching a standard part number formatting template, for example), and/or freeform text entry fields (optionally designated for specific types of information, e.g. a "Problem:" field into which the service engineer is expected to enter a freeform text description of the problem.

The service tag(s) 130 can comprise a label with encoded data 134 disposed thereon. The encoded data 134 can include data related to the servicing of the component 121 of the medical device 120. The encoded data 134 can include, for example, one or more of: an employee identification number of an employee who affixed the service tag 130 to the component 121; and an identification of the service action, a summary of a prior service report 132, or an entire prior service report 132. In some embodiments, the encoded data 134 can be encoded as, for example, a bar code, or a QR code, or can be encoded as stored digital data on a radiofrequency identification (RFID) tag, or on a near-field communication (NFC) tag. In some embodiments, the encoded data 134 can comprise, for example, a uniform resource identifier (URI) linked to the database 111 (i.e., to the service reports 132 stored in the database 111). In addition, the service tag 130 can be color-coded, where the colors of the color code corresponding to an appropriate service action for the component 121.

Encoding the service report 132 and/or other information by way of a URI link or the like can beneficially enable retrieval of more information than can be stored on the service tag 130 itself. On the other hand, the information storage capacity of some encodings such as a QR code is relatively large, e.g. some QR codes can encode several thousand alphanumeric characters (includes punctuation and spaces), and RFID tags and NFC tags can have still larger storage capacities. Accordingly, in some embodiments at least some of the information is directly encoded on the service tag 130 itself. For example, a few thousand alphanumeric characters can be sufficient to store at least a summary of, and possibly the entirety of, a service report 132 for a prior service call. Encoding this information directly onto the service tag 130 can have certain advantages. For example, it enhances data security since the encoded information can be read directly, without resort to electronically accessing a service computer. Additionally, the information directly encoded on the service tag 130 can be selective, e.g. information that may be trade secret or otherwise proprietary may be included in the service report itself but omitted from the summary of the service report that is directly encoded onto the service tag 130. This can be beneficial if it is desired for the service tag 130 to employ an open, nonproprietary architecture that can be read by third party medical device servicing entities. Indeed, if the encoding is nonproprietary then it could also be used by third party servicing entities to install service tags 130, so that relevant service call information is thereby freely shared between different servicing entities (e.g., between the original equipment manufacturer or OEM, and various third party servicing entities) via directly encoded information on service tags affixed to the component. In this open information exchange environment, each servicing entity chooses what information to directly encode on service tags 130 affixed by that servicing entity, so that only information each respective servicing entity wants to share with other servicing entities is included.

In other embodiments, the service tags 130 can be generated before the FSE travels to service the medical device 120 (i.e., if the FSE already knows what the problem is with the medical device 120). Even if the FSE does not know beforehand what the problem is, the service tag 130 can still be generated. In such instances, the service tag 130 would only contain a unique identifier to which the necessary details would have to be linked later whenever these details are known. These links can be stored in the database 111. Prior to visiting a given medical device 120, the FSE could preload all the relevant information that is linked to the service tags 130 that have previously been used for the given medical device 120 on the service device 102, such that remote access to the database 111 would not be needed.

In some embodiments, the component(s) 121 of the medical device 120 can be encoded with basic information in a parts history database 131 implemented in the non-transitory computer readable medium 127. The part history database 131 includes individual records for the component(s) 121, which can be used to update any service tag(s) 130 associated with the component(s) 121, which can be beneficial when printing the service tags 130 prior to the servicing session. The parts history database 131 can be used by servicing entities for similar component(s) 121 in other medical devices 120.

In other embodiments, the service tags 130 can be generated using the service device 102. To do so, the service device 102 can include a printing device 124 (shown diagrammatically in FIG. 1 as a box) configured to print the labels of the service tags 130. In another example, the printing device 124 can be disposed in the same location as the medical device 120, and the FSE can electronically connect with the printing device 124 with the service device 102 to print the service tags 130. The service device 102 can then be used to read the encoded data 134 on the service tag 130 once the service tag 130 is affixed to the component 121 (or alternatively, can be used to read encoded data 134 on a service tag 130 that has been previously applied to the component 121 during a previous service call).

The non-transitory storage medium 107 stores instructions executable by the electronic processor 101 of the service device 102 to perform a method 200 of servicing a component or part 121 of a medical device 120.

Figure 2:
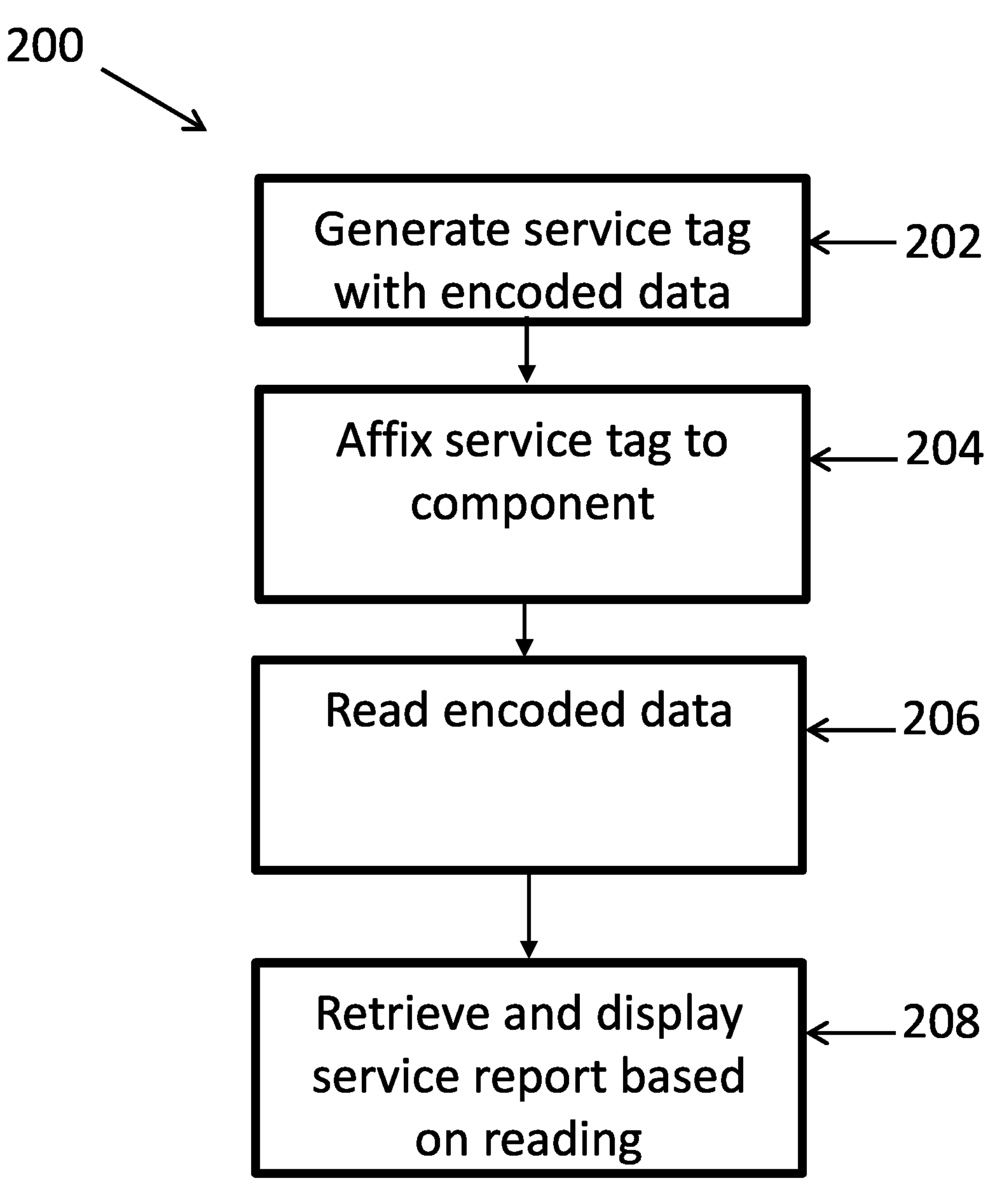
FIG. 2 shows exemplary flow chart operations of the system of FIG. 1.

With continuing reference to FIG. 1 and further reference to FIG. 2, an illustrative embodiment of the method 200 executable by the electronic processor 101 is diagrammatically shown as a flowchart. In some examples, the method 200 may be performed at least in part by cloud processing.

At an operation 202, the service tag 130 having the encoded data 134 is generated. In one example embodiment, the generating operation 202 includes printing the encoded data 134 on a front surface of a label of the service tag 130. The printing can include printing the encoded data 134 on the front side of the label as a bar code or a QR code. In another example embodiment, the service tag 130 comprises a RFID tag or an NFC tag, and the generating operation 202 includes writing the encoded data 134 to the RFID tag 130 or the NFC 130.

In some embodiments, the service tag 130 can be generated as a pre-printed service tag 130 having only a unique identifier, and possibly additionally an identifier of the medical device 120 and the date of visit (i.e., elements that are known prior to the visit), to which the corresponding details on the performed service actions would be linked in the database 111 after the service device 102 has synced with the database 111 at a later stage. This could be preferred whenever the service device 102 has no printing facilities and there is no secure connection available with the remote database 111 during the service call.

At an operation 204, the service tag 130 is affixed to the component 121. In one example embodiment, the service tag 130, as a label, is affixed to the component 121 with an adhesive on the backside of the label. In another example embodiment, the service tag 130, as an RFID tag of an NFC tag, is affixed to the component 121. In a further example embodiment, the service tag 130 is affixed to the component 121 with a fastening mechanism (e.g., plastic zip lock strips, hooks-and-loops, rings, and so forth).

At an operation 206, the encoded data 134 is read using the service device 102. This reading operation 206 can be performed during the current service case of the medical device 120, or can be used to read a service tag 130 affixed to the component 121 from a previous service case.

At an operation 208, based on the reading of the encoded data 134, a service report 132 related to a prior service action for the service tag 130 is retrieved from the database 111. The retrieved service report 132 can then be displayed on the display device 105 of the service device 102. Alternatively, the retrieved service report 132 is selected from all service reports 132 for a given medical device 120 that have been pre-loaded on the service device 102 prior to the service call.

A non-transitory storage medium includes any medium for storing or transmitting information in a form readable by a machine (e.g., a computer). For instance, a machine-readable medium includes read only memory ("ROM"), solid state drive (SSD), flash memory, or other electronic storage medium; a hard disk drive, RAID array, or other magnetic disk storage media; an optical disk or other optical storage media; or so forth.

The methods illustrated throughout the specification, may be implemented as instructions stored on a non-transitory storage medium and read and executed by a computer or other electronic processor.

The disclosure has been described with reference to the preferred embodiments. Modifications and alterations may occur to others upon reading and understanding the preceding detailed description. It is intended that the exemplary embodiment be construed as including all such modifications and alterations insofar as they come within the scope of the appended claims or the equivalents thereof.

The invention claimed is:

1. A medical device maintenance system, comprising:

a secure connection to a medical device wherein information from the medical device is transmitted;

a database storing data transmitted from the medical device;

an interface configured to read any existing service tags on components of the medical device;

an interface for generating a service report which includes information entered by a service engineer, a portion of the information stored in the database that was transmitted from the medical device, and any information read from the existing service tags;

a new service tag generator, where portion of the service report generated are assigned to an associated component based on a relevance to the associated component; and a printing device configured to print a service tag to be affixed to the associated component of an associated medical device, the service tag having encoded data defined by the service tag generator; wherein the service tag is configured to be affixed to the associated component of the associated medical device.

2. The medical device maintenance system of claim 1, wherein the encoded data of the service tag further includes an employee identification number of an employee who affixed the tag to the associated component.

3. The medical device maintenance system of claim 1, wherein the service report generated includes records of new service tags generated for the associated component of the associated medical device.

4. The medical device maintenance system of claim 1, wherein the encoded data of the generated service tag comprises one of: a bar code, a quick response (QR) code, and a radiofrequency identification (RFID) code.

5. The medical device maintenance system of claim 1, wherein the encoded data of the generated service tag comprises a uniform resource identifier (URI) linked to an electronic database.

6. The medical device maintenance system of claim 1, wherein the generated service tag is color-coded based on a corresponding service action for the component.

7. The medical device maintenance of claim 1, wherein the generated service tag includes an adhesive to be affixed to the component.

8. The medical device maintenance system of claim 1, wherein the generated service tag includes a fastening mechanism to be affixed to the associated component.

* * * * *